United States Patent
Gunji

(10) Patent No.: US 9,354,114 B2
(45) Date of Patent: May 31, 2016

(54) SPECTROPHOTOMETER INCLUDING PHOTODIODE ARRAY

(71) Applicant: SHIMADZU CORPORATION, Kyoto-shi, Kyoto (JP)

(72) Inventor: Masahide Gunji, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/083,664

(22) Filed: Nov. 19, 2013

(65) Prior Publication Data

US 2015/0138546 A1  May 21, 2015

(51) Int. Cl.
| | |
|---|---|
| *G01J 3/28* | (2006.01) |
| *G01J 3/18* | (2006.01) |
| *G01J 3/02* | (2006.01) |
| *G01N 30/74* | (2006.01) |
| G01N 21/3577 | (2014.01) |
| G01N 21/85 | (2006.01) |

(52) U.S. Cl.
CPC .............. *G01J 3/2803* (2013.01); *G01J 3/0262* (2013.01); *G01J 3/18* (2013.01); *G01N 30/74* (2013.01); *G01J 2003/2813* (2013.01); *G01N 21/3577* (2013.01); *G01N 21/85* (2013.01)

(58) Field of Classification Search
CPC .............. G01J 3/02; G01J 3/18; G01J 3/2803; G01J 3/2923; G01J 3/28

USPC ................................................... 356/300–334
See application file for complete search history.

(56) References Cited

U.S. PATENT DOCUMENTS

| | | | | |
|---|---|---|---|---|
| 4,844,617 | A * | 7/1989 | Kelderman et al. ........... | 356/624 |
| 5,048,960 | A * | 9/1991 | Hayashi ................. | G01B 11/02 356/319 |
| 5,901,829 | A * | 5/1999 | Ito ...................... | G01R 31/2887 198/345.1 |
| 2006/0263872 | A1* | 11/2006 | Tsukuda .................. | G01J 3/02 435/287.2 |
| 2011/0109903 | A1* | 5/2011 | Lee et al. ...................... | 356/303 |
| 2012/0262711 | A1* | 10/2012 | Oda ........................ | G01N 21/31 356/300 |

FOREIGN PATENT DOCUMENTS

JP          7-318485 A     12/1995

* cited by examiner

*Primary Examiner* — Abdullahi Nur
(74) *Attorney, Agent, or Firm* — Sughrue Mion, PLLC

(57) ABSTRACT

A spectrophotometer in which a normal plane to a diffraction grating is inclined with respect to an optical axis of an incident light passing through a slit, the normal plane to the diffraction grating passing through an intersection point between the optical axis of the incident light i and a grating surface of the diffraction grating. The diffraction grating and a photodiode array PDA are placed such that the photodiode array PDA is parallel to the normal plane to the diffraction grating and that a normal plane to the photodiode array PDA includes a line that is symmetrical to the optical axis of the incident light i about the normal plane to the diffraction grating.

7 Claims, 4 Drawing Sheets

ABSORBANCE SPECTRUM OF CAFFEINE AQUEOUS SOLUTION

SPECTROPHOTOMETER INCLUDING PHOTODIODE ARRAY

TECHNICAL FIELD

The present invention relates to a spectrophotometer including a photodiode array as a detector.

BACKGROUND ART

A photodiode array absorbance detector for a liquid chromatograph has such an apparatus configuration, for example, as is illustrated in FIG. 1, and analyzes a sample that is eluted from a column of the liquid chromatograph and flows into a flow cell.

Light emitted from a light source (L) 13 placed in a light source chamber 12 provided separately from a spectroscopic chamber 11 is focused and applied onto a sample in a flow cell (FC) 15 by an entrance-side concave mirror (M1) 14. At the application point, the light is absorbed at a particular wavelength or wavelengths according to a component or components of the sample, and the resultant light is focused on a slit (S) 17 by an exit-side concave mirror (M2) 16. The light passing through the slit 17 is spectrally separated by a diffraction grating (G) 18, and the intensity is measured for each wavelength by a photodiode array (PDA) 19. In this way, an absorbance spectrum of the analytical sample in the flow cell 15 can be obtained (see, for example, Patent Document 1).

BACKGROUND ART DOCUMENT

Patent Document

[Patent Document 1] JP-A 07-318485

DISCLOSURE OF THE INVENTION

Problems to be Solved by the Invention

Conventionally, the exit point of light from the flow cell 15 (that is, the focusing point of the entrance-side concave mirror 14), the positions of the center of the exit-side concave mirror 16, the center of the slit 17 (that is, the focusing point of the exit-side concave mirror 16), the center of the diffraction grating 18, and the center of the photodiode array 19 are all placed on the same optical plane. A positional relation of the slit 17, the diffraction grating 18, and the photodiode array 19 of these components, which is observed along the optical plane, is illustrated in FIG. 2A.

In this case, there occurs such a phenomenon as illustrated in FIG. 2B in which: a part of a light beam a spectrally separated by the diffraction grating 18 is scattered on the photodiode array, and returns (as a light beam b) again to the diffraction grating 18; and this return light (light beam b) is diffracted by the diffraction grating 18, and is detected (as a light beam c) again by the photodiode array 19. For example, a peak absorbance spectrum by liquid chromatographic analysis using a caffeine aqueous solution as a sample is illustrated in FIG. 7. Although an absorption peak (valley) of the caffeine is supposed to appear at 272 nm, a convex output p is found around 270 nm in an immediate vicinity of 272 nm. As described later, this is an output caused by the light beam c. In this way, the conventional configuration has a problem that the linearity of the absorbance of a sample is deteriorated at a particular wavelength.

The present invention has an object to provide a spectrophotometer that does not cause such a problem that light that has once entered a photodiode array returns to a diffraction grating, and enters the photodiode array again, to thereby decrease the accuracy of spectroscopic measurement.

Means for Solving the Problems

The present invention, which has been made in order to achieve the above-mentioned object, provides a spectrophotometer including: a) a slit; b) a diffraction grating which wavelength-disperses an incident light passing through the slit; and c) a photodiode array including a plurality of light intensity measurement elements arranged in a direction of the wavelength dispersion by the diffraction grating, wherein a normal plane to a grating surface of the diffraction grating is not coincident with a normal plane to the photodiode array, the normal plane to the grating surface passing through an intersection point between an optical axis of the incident light and the grating surface of the diffraction grating.

Here, the grating surface of the diffraction grating refers to a surface formed by a large number of grating lines constituting the diffraction grating. In the case of a planar diffraction grating, the grating surface is a plane. In the case of a concave diffraction grating, the grating surface is concave. Then, a normal plane that passes through a given point of the grating surface thus defined refers to a plane perpendicular to a grating line that passes through the given point.

Further, the normal plane to the photodiode array refers to a plane that passes through a line connecting the centers of the plurality of light intensity measurement elements included in the photodiode array (this line is referred to as the central line of the photodiode array), and refers to a plane perpendicular to surfaces of the light intensity measurement elements.

In the spectrophotometer according to the present invention, the light passing through the slit is wavelength-dispersed by the diffraction grating, and the intensity is measured for each wavelength by each of the light intensity measurement elements in the photodiode array. Here, a part of the light that has entered the photodiode array is reflected by its surface to return toward the diffraction grating. This state is described with reference to FIG. 3A to FIG. 3D. Note that, in FIG. 3A to FIG. 3D, a plurality of light intensity measurement elements are arranged in a photodiode array PDA in a direction perpendicular to the figure plane.

In a conventional spectrophotometer, as illustrated in FIG. 3A, a diffraction grating G and the photodiode array PDA are placed such that a normal plane α to a grating surface of the diffraction grating G is coincident with a normal plane β to the photodiode array PDA. Hence, a light beam that has entered the photodiode array PDA from the diffraction grating G (as a light beam a) and has been reflected by a surface of the photodiode array PDA returns to the diffraction grating G (as a light beam b), is reflected thereon and diffracted thereby, and enters the photodiode array PDA again (as a light beam c). In comparison, according to the spectrophotometer according to the present invention, the following three cases are possible for the placement of the diffraction grating G and the photodiode array PDA.

(1) The case where the light beam a from the diffraction grating reaches the photodiode array PDA along the normal plane α to the grating surface of the diffraction grating G (FIG. 3B)

In this case, the photodiode array PDA exits on the normal plane α to the grating surface of the diffraction grating G. Because the normal plane β to the photodiode array PDA is not coincident with the normal plane α to the grating surface, the light beam a that has entered a surface of each of the light intensity measurement elements in the photodiode array PDA is reflected toward a direction different from the light entrance direction (toward a direction symmetrical about the normal plane β to the photodiode array PDA). The travelling direction of the reflected light beam b is different from the normal plane α to the diffraction grating G. Hence, even if the light beam b that has returned to the diffraction grating G is diffracted and reflected by the diffraction grating G, the resultant light beam c does not return to the photodiode array PDA. Note that an incident light beam i reaches the diffraction grating from the slit, on the normal plane α to the grating surface of the diffraction grating G.

(2) The case where the light beam a from the diffraction grating G reaches the photodiode array PDA along the normal plane β to the photodiode array PDA (FIG. 3C)

In this case, the light beam b reflected by the surface of the photodiode array PDA returns to the diffraction grating G along the normal plane β to the photodiode array PDA, but the light beam c diffracted and reflected by the diffraction grating G does not return to the photodiode array PDA. Note that the incident light beam i enters the diffraction grating G in a direction symmetrical about the normal plane α to the grating surface of the diffraction grating G.

(3) The case where the light beam a from the diffraction grating G reaches the photodiode array PDA on a plane different from both the normal plane α to the grating surface and the normal plane β to the photodiode array PDA (FIG. 3D)

In this case, the light beam a that has entered the surface of each of the light intensity measurement elements in the photodiode array PDA is reflected toward a direction different from the light entrance direction (toward a direction symmetrical about the normal plane β to the photodiode array PDA). The travelling direction of the reflected light beam b is different from the normal plane α to the diffraction grating G. Hence, even if the light beam b that has returned to the diffraction grating G is diffracted and reflected by the diffraction grating G, the resultant light beam c does not return to the photodiode array PDA. Also in this case, the incident light beam i enters the diffraction grating G in a direction symmetrical about the normal plane α to the grating surface of the diffraction grating G.

Effects of the Invention

In the spectrophotometer according to the present invention, even if a part of light that has been wavelength-dispersed by the diffraction grating and has entered the surface of the photodiode array is reflected by the surface, the part of the light is prevented from returning again to the photodiode array after being reflected and diffracted by the grating surface of the diffraction grating. Hence, high-accuracy spectroscopic measurement can be performed for every wavelength.

MODE FOR CARRYING OUT THE INVENTION

Figure 4:
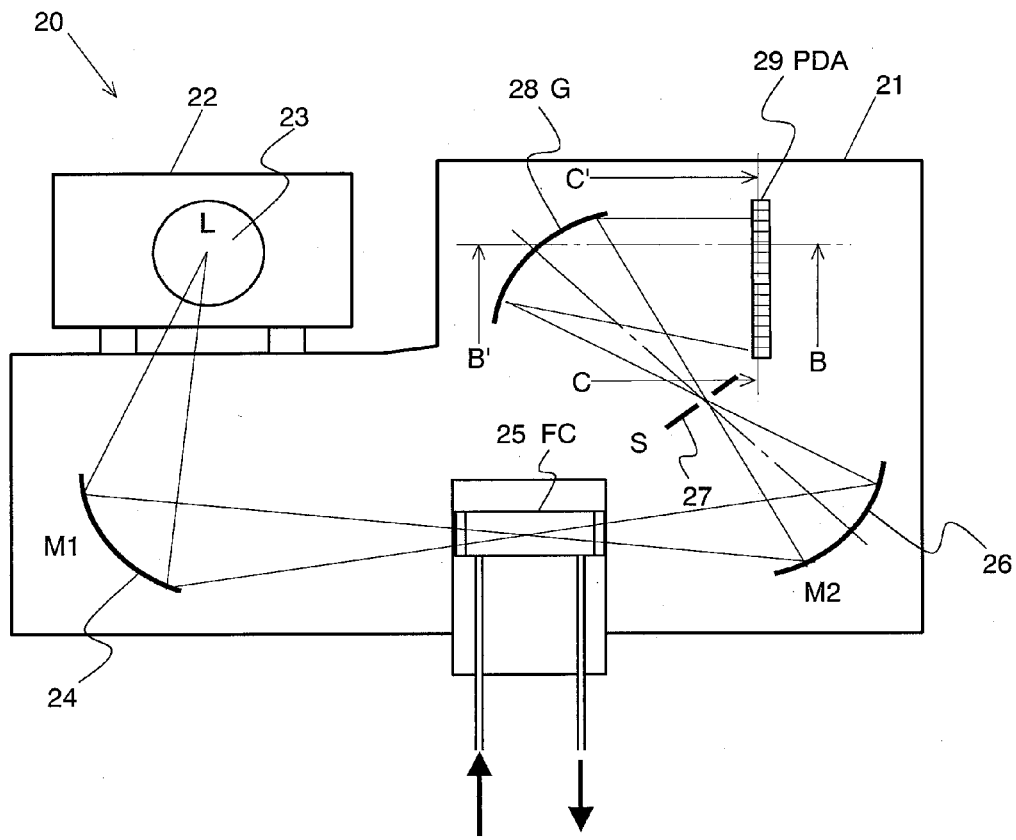
FIG. 4 is a schematic configuration diagram of a photodiode array absorbance detector for a liquid chromatograph according to an embodiment of the present invention.

A photodiode array absorbance detector 20 for a liquid chromatograph including a spectrophotometer according to the present invention is described as an embodiment of the present invention. In the photodiode array absorbance detector 20 for the liquid chromatograph according to the present embodiment, as illustrated in FIG. 4, light emitted from a light source (L) 23 placed in a light source chamber 22 provided separately from a spectroscopic chamber 21 is focused and applied onto a flow cell (FC) 25 by an entrance-side concave mirror (M1) 24. At the application point, the light is temporally separated by the liquid chromatograph (not illustrated), and is absorbed at a particular wavelength or wavelengths according to a component or components of a sample that flows into the flow cell 25, and the resultant light is focused on a slit (S) 27 by an exit-side concave mirror (M2) 26. The light passing through the slit 27 is spectrally separated by a diffraction grating (G) 28, and the intensity is measured for each wavelength by a photodiode array (PDA) 29.

Figure 1:
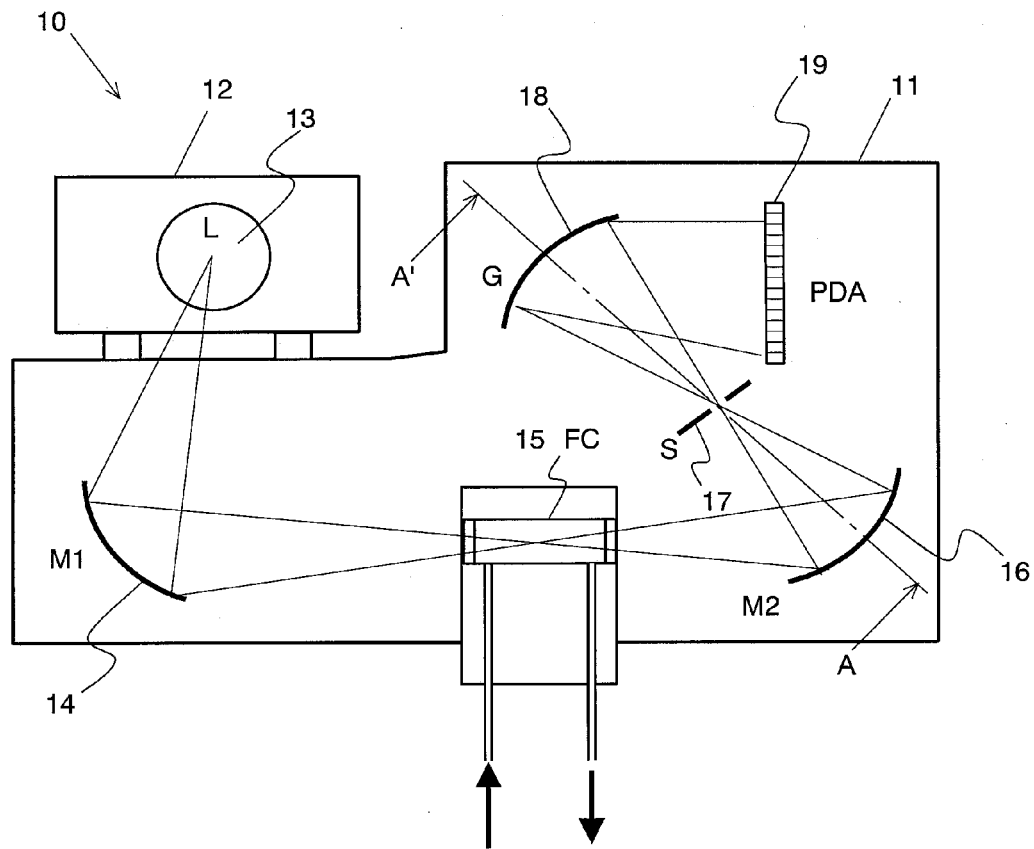
FIG. 1 is a schematic configuration diagram of a conventional photodiode array absorbance detector for a liquid chromatograph.
Figure 2A:
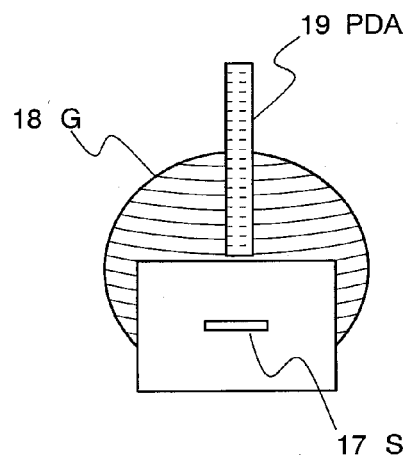
FIG. 2A is a diagram of a positional relation of a slit, a diffraction grating, and a photodiode array in the conventional photodiode array absorbance detector for the liquid chromatograph, which is observed along an incident light-diffracted light plane.
Figure 2B:
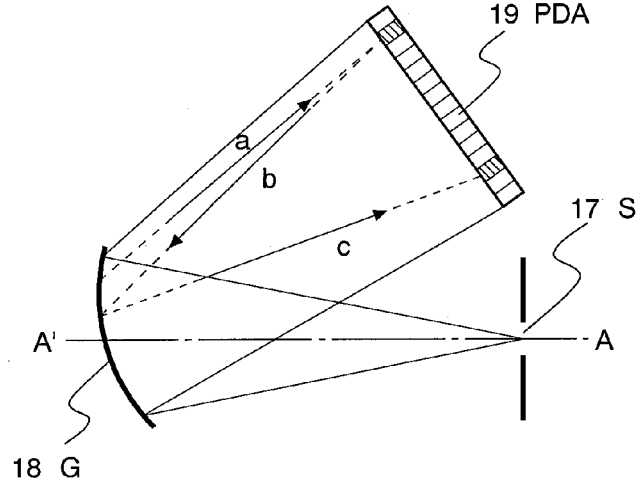
FIG. 2B is a diagram of the positional relation of the slit, the diffraction grating, and the photodiode array in the conventional photodiode array absorbance detector for the liquid chromatograph, which is observed in a direction perpendicular to the incident light-diffracted light plane.
Figure 3A:
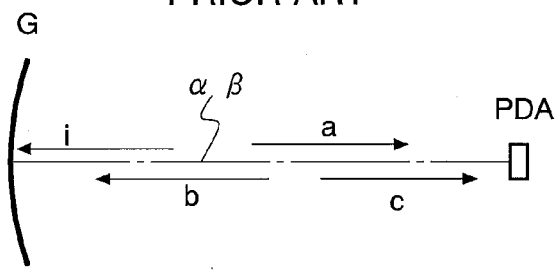
FIG. 3A is a schematic configuration diagram of a positional relation of a diffraction grating and a photodiode array in a conventional spectrophotometer, which is observed in a direction parallel to the central line of the photodiode array.
Figure 3B:
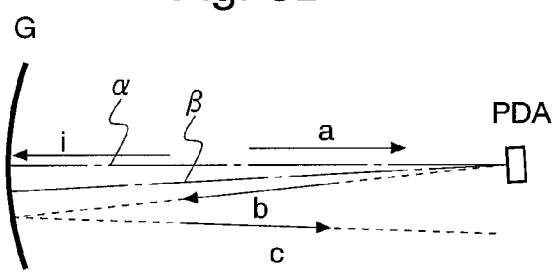
FIG. 3B is a schematic configuration diagram of a positional relation of a diffraction grating and a photodiode array in a first mode of a spectrophotometer according to the present invention, which is observed in a direction parallel to the central line of the photodiode array.
Figure 3C:
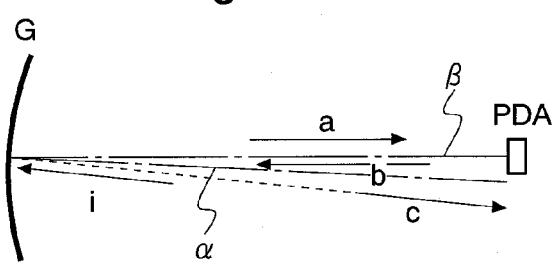
FIG. 3C is a schematic configuration diagram of a positional relation of a diffraction grating and a photodiode array in a second mode of the spectrophotometer according to the present invention, which is observed in a direction parallel to the central line of the photodiode array.
Figure 5A:
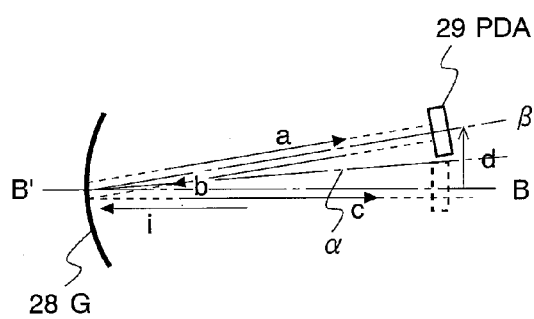
FIG. 5A is a schematic configuration diagram of a positional relation of a diffraction grating and a photodiode array in the photodiode array absorbance detector for the liquid chromatograph according to the embodiment, which is observed in a direction parallel to the central line of the photodiode array.

Here, in the photodiode array absorbance detector 20 according to the present embodiment, unlike a conventional one illustrated in FIG. 1, the photodiode array 29 is moved parallel by a distance d in a direction perpendicular to the plane of FIG. 4 (and FIG. 1). The distance d is set to be equivalent to (once as large as) or more than the width of the photodiode array 29 (the dimension of the photodiode array in a direction orthogonal to its central line) (FIG. 6; note that, in FIG. 6, Cz-C' represents the central line). A normal plane α to the diffraction grating 28 is accordingly inclined in the direction perpendicular to the figure plane, and the diffraction grating 28 and the photodiode array 29 are placed such that light passing through the slit 27 and has entered the diffraction grating 28 along an optical axis i enters the photodiode array 29. This state is illustrated in FIG. 5A. In this example, a normal plane β to the photodiode array 29 is also inclined so as to face the diffraction grating 28. This state corresponds to the case (FIG. 3C) in (2) described above.

Figure 6:
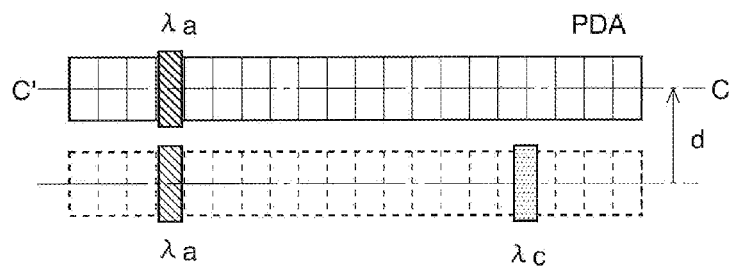
FIG. 6 is a schematic configuration diagram illustrating a position of the diffraction grating in the photodiode array absorbance detector for the liquid chromatograph according to the embodiment, in comparison with a conventional case.
Figure 7:
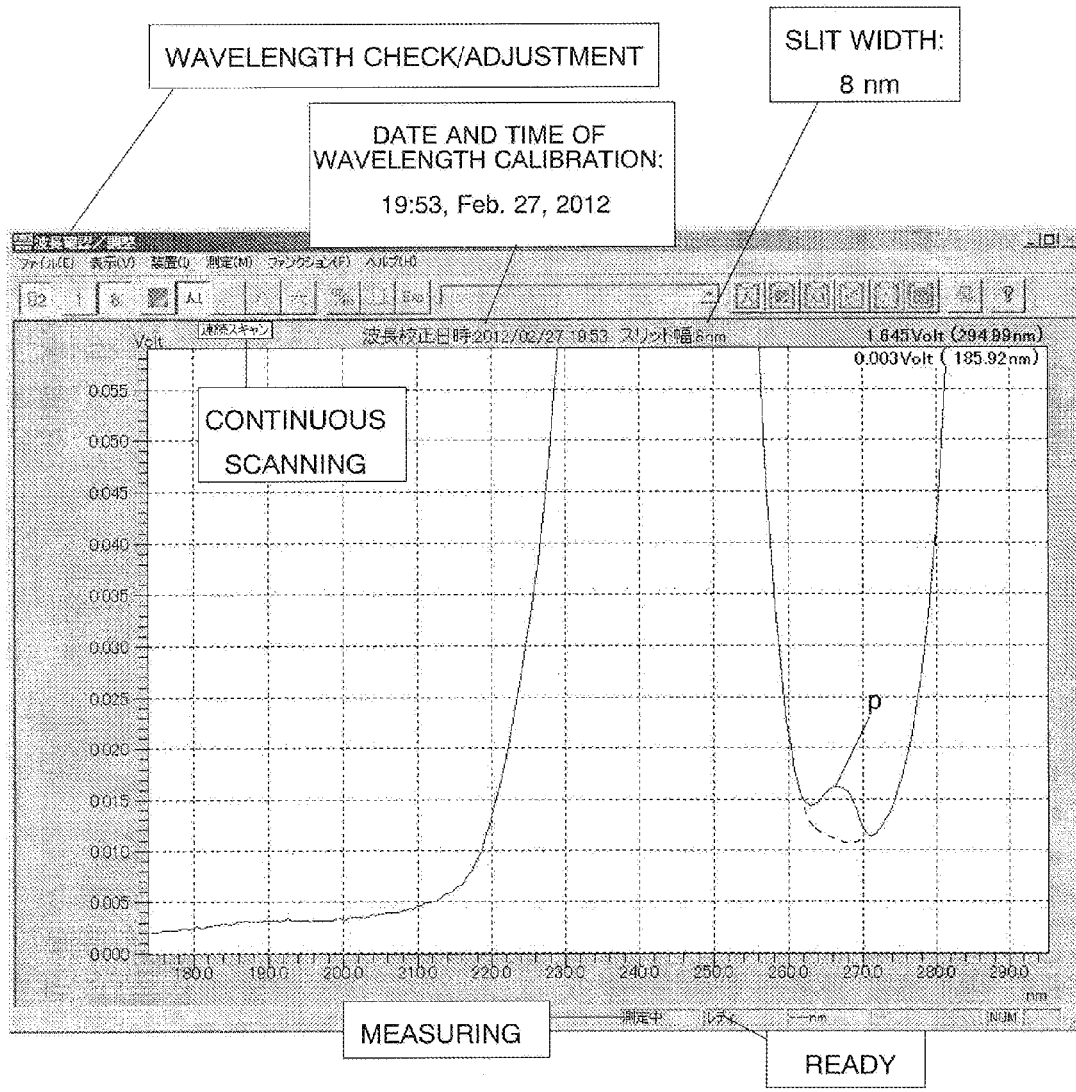
FIG. 7 is a spectrum diagram of a caffeine aqueous solution, illustrating the state where a stray light peak that appears in the conventional photodiode array absorbance detector for the liquid chromatograph disappears according to the present invention.

With this configuration, as illustrated in FIG. 6, even if a light beam with a wavelength λa that has been spectrally separated by the diffraction grating 28 and has entered the photodiode array 29 is reflected by its surface to return to the diffraction grating 28, the light beam does not return again to the photodiode array 29 unlike the conventional case (dotted lines). As a result, it is confirmed that the convex part p in the spectrum (FIG. 7) of the caffeine aqueous solution described above, which is caused by stray light occurring in the conventional technique, disappears and that an absorption peak (valley) of the caffeine correctly appears in the vicinity of 272 nm as indicated by a dotted line. That is, it is confirmed that the present invention enables accurate light intensity measurement for every wavelength of a measurement region.

Figure 3D:
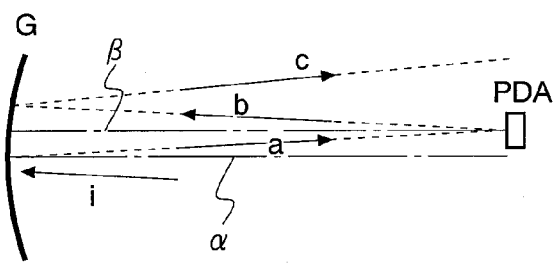
FIG. 3D is a schematic configuration diagram of a positional relation of a diffraction grating and a photodiode array in a third mode of the spectrophotometer according to the present invention, which is observed in a direction parallel to the central line of the photodiode array.
Figure 5B:
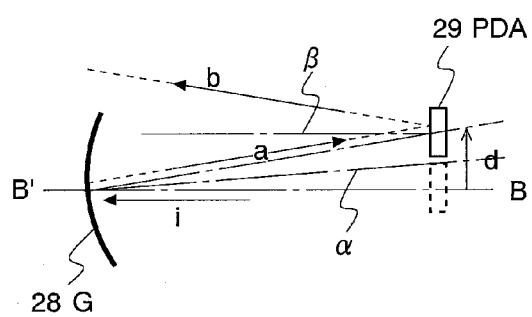
FIG. 5B is a schematic configuration diagram of another positional relation of the diffraction grating and the photodiode array in the photodiode array absorbance detector for the liquid chromatograph according to the embodiment, which is observed in a direction parallel to the central line of the photodiode array.

Note that, as illustrated in FIG. 5B, the photodiode array 29 may be simply moved by the distance d without changing its inclination (orientation). That is, the photodiode array 29 is moved parallel by the distance d while the normal plane α to a grating surface of the diffraction grating is kept parallel to the normal plane β to the photodiode array. This corresponds to the case (FIG. 3D) in (3) described above. Also in this case, a light beam a that has entered the photodiode array 29 from the diffraction grating 28 is reflected by its surface (to become a light beam b), and the light beam b is not applied to the diffraction grating 28. Further, even if the light beam b is applied to the diffraction grating 28, the light beam b does not return again to the photodiode array 29.

In the above-mentioned embodiment, description is given of the case where the diffraction grating is a concave diffraction grating, but the present invention can also be applied to a plane diffraction grating. If an appropriate optical system is set, high-accuracy spectroscopic measurement can be performed by using the principle of the present invention.

EXPLANATION OF NUMERALS 10, 20 . . . Photodiode Array Absorbance Detector
11, 21 . . . Spectroscopic Chamber
12, 22 . . . Light Source Chamber
13, 23 . . . Light Source
14, 24 . . . Entrance-Side Concave Mirror (M1)
15, 25 . . . Flow Cell (FC)
16, 26 . . . Exit-Side Concave Mirror (M2)
17, 27 . . . Slit (S)
18, 28 . . . Diffraction Grating (G)
19, 29 . . . Photodiode Array (PDA)
α . . . Normal Plane to Grating Surface of Diffraction Grating
β . . . Normal Plane to Photodiode Array

The invention claimed is:

1. A spectrophotometer comprising:
a) a slit;
b) a diffraction grating which wavelength-disperses an incident light passing through the slit; and
c) a photodiode array including a plurality of light intensity measurement elements arranged in a direction of the wavelength dispersion by the diffraction grating, wherein
a first plane which is perpendicular to a grating line and passes through an intersection point between an optical axis of the incident light and a grating surface of the diffraction grating is not coincident with a second plane which is perpendicular to surfaces of the light intensity measurement elements and passes through a central line of the photodiode array;
wherein the central line of the photodiode array is a line connecting centers of the plurality of light intensity measurement elements.

2. The spectrophotometer according to claim 1, wherein the diffraction grating and the photodiode array are placed such that light from the diffraction grating reaches the photodiode array along the first plane.

3. The spectrophotometer according to claim 1, wherein the diffraction grating and the photodiode array are placed such that light from the diffraction grating reaches the photodiode array along the second plane.

4. A spectrophotometer comprising:
a) a slit;
b) a diffraction grating which wavelength-disperses an incident light passing through the slit; and
c) a photodiode array including a plurality of light intensity measurement elements arranged in a direction of the wavelength dispersion by the diffraction grating, wherein
a first plane which is perpendicular to a grating line and passes through an intersection point between an optical axis of the incident light and a grating surface of the diffraction grating is inclined with respect to the optical axis of the incident light passing through the slit, and
the diffraction grating and the photodiode array are placed such that the photodiode array is parallel to the first plane and that a second plane which is perpendicular to surfaces of the light intensity measurement elements and passes through a central line of the photodiode array includes a line that is symmetrical to the optical axis of the incident light about the first plane;
wherein the central line of the photodiode array is a line connecting centers of the plurality of light intensity measurement elements.

5. The spectrophotometer according to claim 4, wherein a distance between the central line of the photodiode array and the first plane is equal to or more than a width of the photodiode array.

6. A spectrophotometer comprising:
a) a slit;
b) a diffraction grating which wavelength-disperses an incident light passing through the slit; and
c) a photodiode array including a plurality of light intensity measurement elements arranged in a direction of the wavelength dispersion by the diffraction grating, wherein
a first plane which is perpendicular to a grating line and passes through an intersection point between an optical axis of the incident light and a grating surface of the diffraction grating is inclined with respect to the optical axis of the incident light passing through the slit, and
the diffraction grating and the photodiode array are placed such that a second plane which is perpendicular to surfaces of the light intensity measurement elements and passes through a central line of the photodiode array is parallel to the first plane;

wherein the central line of the photodiode array is a line connecting centers of the plurality of light intensity measurement elements.

7. The spectrophotometer according to claim 6, wherein a distance between the central line of the photodiode array and the first plane is equal to or more than a width of the photodiode array.

* * * * *